US006939374B2

(12) United States Patent
Banik et al.

(10) Patent No.: US 6,939,374 B2
(45) Date of Patent: Sep. 6, 2005

(54) STENTS, STENTING SYSTEMS, AND RELATED METHODS FOR AGENT DELIVERY

(75) Inventors: Michael S. Banik, Bolton, MA (US); Kurt Geitz, Sudbury, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 525 days.

(21) Appl. No.: 10/024,261

(22) Filed: Dec. 21, 2001

(65) Prior Publication Data

US 2003/0120339 A1 Jun. 26, 2003

(51) Int. Cl.[7] ................................................. A61F 2/06
(52) U.S. Cl. ..................................... 623/1.27; 606/194
(58) Field of Search ............................... 606/108, 191, 606/194, 198; 623/1.15, 1.16, 1.39, 1.27, 1.46, 1.44

(56) References Cited

U.S. PATENT DOCUMENTS

| 4,649,914 A | * | 3/1987 | Kowalewski | .......... 128/207.15 |
| 5,024,671 A | * | 6/1991 | Tu et al. | .................... 623/1.54 |
| 5,229,045 A | * | 7/1993 | Soldani | ....................... 264/41 |
| 5,328,470 A | | 7/1994 | Nabel et al. | |
| 5,411,550 A | * | 5/1995 | Herweck et al. | .......... 623/1.27 |
| 5,439,446 A | | 8/1995 | Barry | |
| 5,549,675 A | | 8/1996 | Neuenfeldt et al. | |
| 5,628,784 A | | 5/1997 | Strecker | |
| 6,146,389 A | * | 11/2000 | Geitz | ......................... 606/108 |
| 6,805,703 B2 | * | 10/2004 | McMorrow | ................ 623/1.11 |

FOREIGN PATENT DOCUMENTS

WO    WO 92/11895    7/1992

* cited by examiner

Primary Examiner—Julian W. Woo
Assistant Examiner—Victor Nguyen
(74) Attorney, Agent, or Firm—Finnegan, Henderson, Farabow, Garrett, & Dunner, L.L.P.

(57) ABSTRACT

A stenting system for insertion into the lumen of a body duct or vessel for delivering a therapeutic agent to a treatment site on the duct or vessel. The stenting system includes an a tubular stent member having a lumen there through to allow the passage of material, an outer membrane attached to the stent at least a portion of which is porous to the therapeutic agent to allow the agent to pass to the treatment site, an inner membrane attached to the stent which is nonporous to the therapeutic agent to prevent the agent from entering the lumen of the stent, and a chamber located between the inner and outer membranes for holding the therapeutic agent. The therapeutic agent in the chamber may diffuse through the porous portion of the membrane and be deposited directly on the body site.

22 Claims, 3 Drawing Sheets

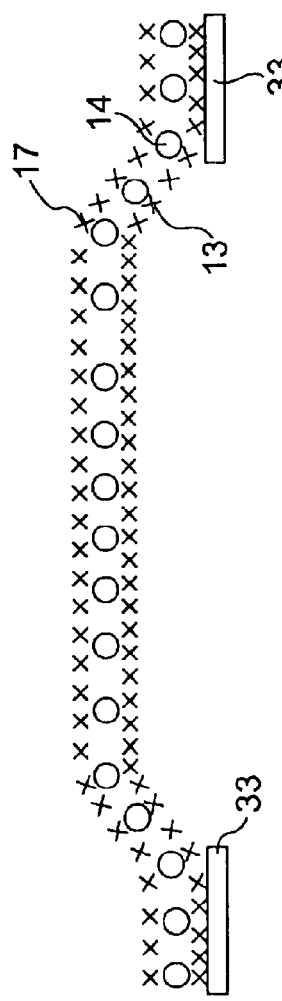
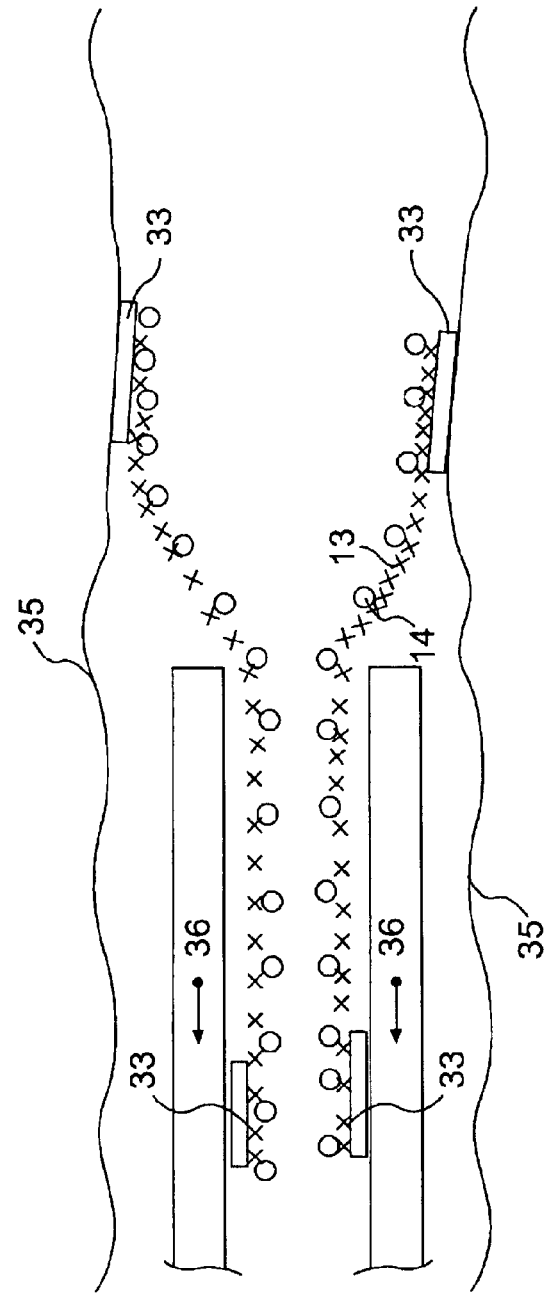

STENTS, STENTING SYSTEMS, AND RELATED METHODS FOR AGENT DELIVERY

DESCRIPTION OF THE INVENTION

1. Field of the Invention

The present invention relates to a stenting system and, more particularly, to a stenting system for delivering therapeutic agents to body sites. Still more particularly, the present invention relates to a stenting system for delivering cellular fluids or other agents to the walls of a body lumen over a period of time.

2. Background of the Invention

In general, infusion techniques are used to deliver a therapeutic agent to the body. For many medical applications, it is desirable to deliver therapeutic agents, such as drugs or cellular fluids containing cultured cells, directly to a treatment site, such as a duct, vessel, or other organ, rather than through general systemic administration.

For example, it may be desirable to treat a duct or organ that has developed pre-cancerous or cancerous cells directly with a cellular or other therapeutic agent. One such example is in the case of Barret's esophagus wherein the cell morphology on the surface of the esophagus has changed as a result of chronic gastric reflux of gastric content and acids into the esophagus. This change in cell morphology is one indicator of potential esophageal cancer. It would be desirable to have a system that treats these cells locally and directly with cultured normal cells to develop normal esophageal cell type.

It may also be desirable to treat other diseased tissues locally and directly. For instance, some treatments involve using steroidal or nonsteroidal anti-inflammatory agents, such as in the case of Crohn's disease which causes inflammation in the colon, and inflammatory bowel disease. Treatment of the inflamed organs could be more effective if the treatment was delivered and deposited directly to the target site.

As well, direct apposition of therapeutic agents could reduce the amount of agents that are unnecessarily delivered to the rest of the body and reduce the amount of side effects that may result from the treatment. In addition, because the wall of the vessel to be treated may be weakened by disease or other trauma, it may be desirable to support or protect the vessel wall as the therapeutic agent is delivered.

Moreover, in many cases, it is desirable to deliver the therapeutic material over a long or indefinite period of time. Thus, it may be desirable to have a delivery system that does not occlude the target vessel and can remain at the target site over a long period of time.

SUMMARY OF THE INVENTION

Objects and advantages of the invention will be set forth in the description which follows and, in part, will be obvious from the description or may be learned by practice of the invention. The objects and advantages of the invention will be realized and attained by means of the elements and combinations particularly pointed out in the appended claims.

To achieve the objects and in accordance with the purpose of the invention, as embodied and broadly described herein, the invention includes a stenting system for insertion into a body lumen for delivering a therapeutic agent to a site on the body lumen. The stenting system may include a tubular member having a lumen there through to allow the passage of material, wherein the tubular member may be expanded causing the stenting system to be retained against the wall of the body lumen; an outer membrane surrounding the tubular member, wherein at least a portion of the outer membrane is porous to the therapeutic agent to allow the therapeutic agent to be deposited on the site; an inner membrane attached to the tubular member, wherein the inner membrane is non-porous to the therapeutic agent to be delivered to the site; and a chamber located between the inner and outer membranes for holding the therapeutic agent, wherein the therapeutic agent in the chamber diffuses through the porous portion of the outer membrane and is deposited directly on the body site.

According to embodiments of the invention, the stenting system may include an inner tubular member having a lumen there through for the passage of material; a membrane surrounding the inner tubular member; an outer tubular member surrounding the inner tubular member and the membrane; and a porous member forming at least a portion of the outer tubular member, wherein the membrane and the outer tubular member define a chamber there between for holding the therapeutic agent, wherein the therapeutic agent in the chamber may pass through the porous member of the outer tubular member and be deposited directly on the body site, and wherein the membrane is non-porous to the therapeutic agent thereby isolating the lumen of inner tubular member from the therapeutic agent in the chamber.

According to further embodiments of the invention, the stenting system may include an expandable tube having a lumen there through, wherein the sides of the tube have openings therein to allow passage of the therapeutic agent to the body site; an outer membrane surrounding the expandable tube and forming a chamber with the surface of the expandable tube, wherein at least a portion of the membrane being porous to the therapeutic agent allowing diffusion of the therapeutic agent there through to the body site and wherein the expandable tube prevents the therapeutic agent from diffusing from the chamber and into the lumen of the expandable tube; and an opening in the chamber allowing delivery of the therapeutic agent to the chamber, wherein the therapeutic agent delivered to the chamber diffuses through the porous portion of the outer membrane and is deposited on the body site.

It is to be understood that both the foregoing general description and the following detailed description are exemplary and explanatory and are not restrictive of the invention as claimed.

BRIEF DESCRIPTION OF THE DRAWINGS

The accompanying drawings are included to provide a further understanding of the invention and are incorporated in and constitute a part of this specification. The drawings illustrate embodiments of the invention and, together with the description, serve to explain the principles of the invention.

FIG. 6 is a cross-sectional side view of another stenting system according to an embodiment of the present invention.

FIG. 7. is a cross-sectional side view of the stenting system of FIG. 6 being delivered to a target site, according to an embodiment of the present invention.

DESCRIPTION OF THE EMBODIMENTS

Figure 1:
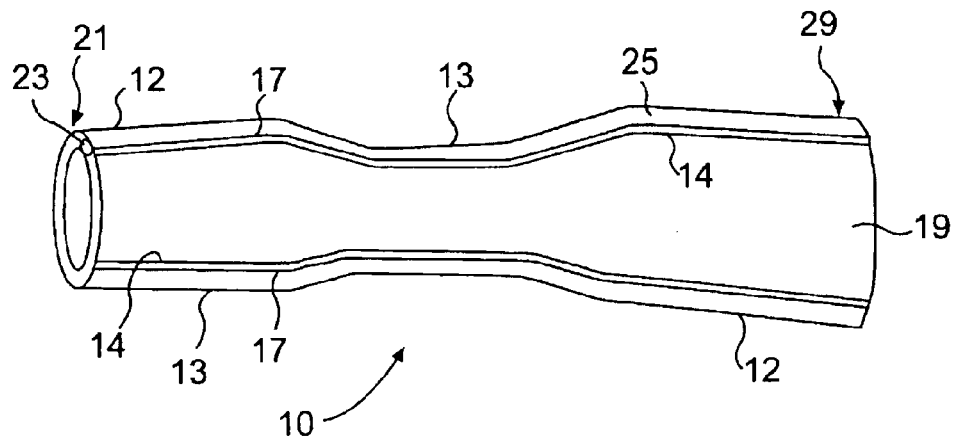
FIG. 1 is a sectional side view of a stenting system according to a preferred embodiment of the present invention.

Reference will now be made in detail to the present preferred embodiments of the invention, examples of which are illustrated in the accompanying drawings. Wherever possible, the same reference numbers are used in the drawings and the description to refer to the same or like parts.

The present invention is directed to systems and methods for delivering a therapeutic agent to a body duct, vessel, organ, or other body cavity or lumen within the body. The present invention generally includes an expandable stenting system that can be delivered to the lumen of a body duct and expanded to retain the stenting system in the duct and support and/or protect the walls of the duct. The stenting system includes a tubular member, such as a stent, and inner and outer membranes forming a chamber there between for holding the therapeutic agent. At least a portion of the outer membrane is formed from a porous material forming a porous membrane. Because the porous membrane of the stenting system is directly adjacent to the target vessel or organ when installed, the therapeutic agent may be delivered directly to and deposited directly on the target site. Moreover, the stenting system can be left in place for an indefinite period of time because material, including blood, food, or other material, may pass through the stent. Because the stenting system can remain in place for an indefinite period of time, as opposed to a balloon or other such delivery mechanism, the therapeutic agent can advantageously be delivered over a long period of time if necessary.

The stenting systems allow for direct and controlled release of cellular or therapeutic material over time or for immediate delivery. The membranes of the stenting system can allow a wide range of materials to be deposited or seeded to the treatment site, including cellular solutions, drugs, or other treatment material. For instance, the stenting systems according to embodiments of the present invention may be used to deliver epithelial cell culture to an area of the esophagus that has been ablated from photo therapy or other cellular destructive techniques. The stenting systems according to embodiments of the present invention provide a mechanism for delivery of cultured cells or other therapeutic agents to the site of the destroyed cells thereby seeding healthy cells onto an area having damaged cells. The stenting system protects the tissue or cellular area from further damage or cell erosion, while providing a mechanism to further treat the site.

The stenting systems according to other embodiments of the present invention may be used to deliver other therapeutic agents to the site. For instance, the stenting systems may be used to deliver cancer treating drugs to the site of a cancerous or precancerous lesion, or may be used to deliver anti-inflammatory or other agents to a site. The stenting systems may allow for repeated treatments or agents to be delivered as desired to achieve the outcome desired. The stenting systems may be removable such that they may be removed once the cell growth process has been completed, the tissue has healed, or the treatment has otherwise been completed.

Figure 2:
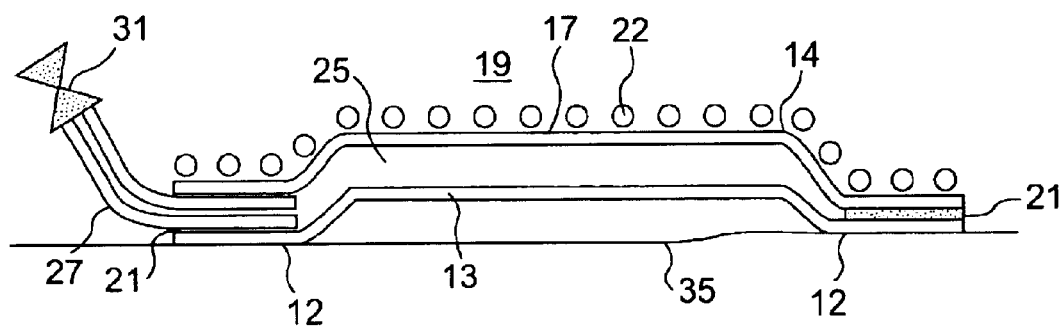
FIG. 2 is a cross-sectional side view of a portion of the stenting system of FIG. 1. in a body vessel.

Referring to FIGS. 1 and 2, an exemplary stenting system of the present invention is shown generally at 10. Stenting system 10 is delivered to the target site, shown as vessel wall 35 in FIG. 2. Stenting system 10 includes a tubular member, an outer membrane 13, an inner membrane 17, and a chamber 25 between membrane 13 and 17 for holding the therapeutic agent. The tubular member is preferably stent 14 having a lumen 19. Preferably, the outer membrane 13 allows passage of the therapeutic agent to the treatment site, and inner member 17 prevents passage of the therapeutic agent into lumen 19 of the stent 14.

Membrane 13 is designed to allow the therapeutic agent, such as cellular material or agents, to reach the treatment site, and preferably surrounds the outer surface of stent 14, or at least some portion thereof. To facilitate delivery of the therapeutic agent, at least a portion of membrane 13 is porous to the therapeutic agent, allowing the agent to diffuse through membrane 13 to the target site. Because membrane 13 is directly adjacent the vessel wall, the therapeutic material is brought into direct contact with the target vessel and the effectiveness of the treatment is increased. As well, the amount of agent diffused to the surrounding tissue or the circulatory, digestive, or other bodily system is minimized, thereby decreasing the amount of agents that reach healthy tissue.

Membrane 13 is preferably porous over most or all of its surfaces to allow even distribution of the therapeutic agent across the wall of the target vessel. It may be desirable, however, in certain applications for less than the entire surface of membrane 13 to be porous. For example, it may be desirable when administering a toxic substance to a tumor to have only the portion of membrane 13 directly adjacent the tumor be porous. Similarly, in other circumstances it may be desirable to treat only a portion of the tissue adjacent the stenting system.

Figure 3:
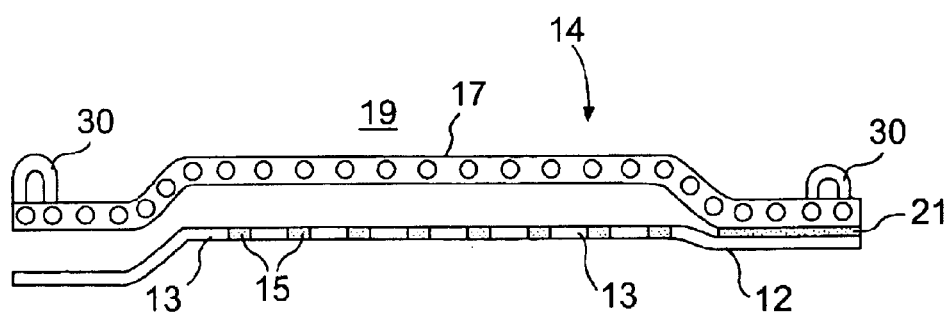
FIG. 3 is a cross-section side view of a portion of another stenting system according to an embodiment of the present invention.

Membrane 13 may be porous due to micro holes 15 within the membrane, as shown in FIG. 3 for example. The porosity of the membrane can be thereby controlled by the size of holes 15 and adapted to the treatment. Preferably, membrane 13 is permeable to oxygen, nitrogen, carbon dioxide and water, as well as the therapeutic agent to be delivered. For instance, in the case of treatment using cellular material as the therapeutic agent, membrane 13 should be permeable to cells of a size of approximately 25 micrometers. As previously stated, however, it should be recognized that the desired porosity of the membrane depends on the treatment being performed and could be adapted to various treatments. Moreover, by controlling the size of holes 15, membrane 13 can provide a controlled release of the therapeutic agent.

Membrane 13 is preferably elastomeric, allowing it to conform to the lumen or organ walls for greater apposition of the therapeutic agent to the target site and less damage to the target site. Materials providing suitable porosity and softness include polyolefin, polypropylene, polyethylene, and polycarbonate. Membrane 13 may be spun from these materials and the porosity selected based on the treatment to be performed. Other suitable materials that provide the appropriate porosity may be used. Alternatively, micro holes could be provided in more rigid material, such as silicon or polyurethane, or rubber, such as ethylene vinyl acetate, through drilling with a laser or otherwise or other method of providing small precise holes. Outer member 13 could be a rigid or expandable tubular member.

Figure 4:
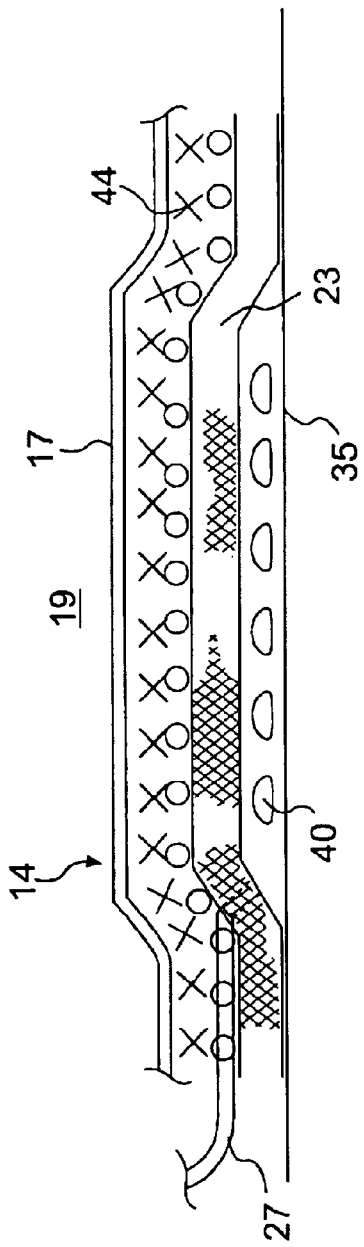
FIG. 4 is a cross-sectional side view of a portion of another stenting system according to a further embodiment of the present invention.

As an alternative, the outer membrane may be made porous by a loose mesh construction as shown at 23 in FIG. 4. In this case, stent 14 is shown embedded in a mesh membrane 44 and membrane 17 is located on the inner surface of stent 14. Cells or other therapeutic agents are shown at 40 between the stenting system and vessel wall 35. Further, membranes 13 and 23 may be coated or impregnated with hyaluranic acid or other suitable substance to prevent tissue growth into the membrane.

Membrane 13 may be adhesively bound to membrane 17 and stent 14 as shown in FIGS. 2 and 3 or can be attached to membrane 17 and stent 14 through other suitable means. As shown in FIG. 2, membrane 13 may be adhered directly to inner member 17 at one end and adhered to a flexible tubing 27, which allows for the passage of the therapeutic agent. Adhesive 21 may be applied at the ends 12 of membrane 13. The adhesive portions attaching membrane 13 to membrane 17 and tubing 27 preferably render membrane 13 non-porous at ends 12 such that the therapeutic agent cannot pass through membrane 13 in the areas of the adhesive portions at ends 12. It should be recognized that membrane 13 may be attached or secured to either or both of membrane 17 or stent 14 at each end, attached to tubing at each end, or otherwise attached to structure that forms chamber 25 between membrane 13 and 17.

Inner membrane 17 preferably is designed to prevent the therapeutic agent from passing into lumen 19 of stent 14. As a result, membrane 17 is preferably non-porous to the therapeutic agent. Membrane 17 is also preferably elastomeric and permeable to oxygen, nitrogen, and carbon dioxide while being non-permeable to HCL and hydrogen ions. Membrane 17 should further be non-reactive to acid and non-toxic. Suitable materials include butadiene or ethylene vinyl chloride, or other appropriate materials. Alternatively, membrane 17 could be non-permeable to all fluids and gas, and made from silicon, polyurethane, or other suitable material.

Membrane 17 may be adhesively bonded to stent 14 by adhesive 22, as shown in FIG. 2, or attached to stent 14 through other suitable mechanisms. While membrane 17 is shown attached to the outer surface of stent 14, it should be recognized that membrane 17 could be located on the inner surface of stent 14 or that stent 14 could be embedded in membrane 17, as shown in FIG. 3. Alternatively, it could be possible to eliminate membrane 17 if the walls of stent 14 are solid with no openings, thereby preventing the therapeutic agent from entering lumen 19.

Membrane 17 also preferably is bonded to membrane 13 at one end of stent 14 and bonded to tubing 27 at the other end of stent 14, as shown in FIG. 2. As described above, it should be recognized that membrane 17 can be attached to membrane 13 at each end, attached to tubing at each end, or otherwise attached to structure that forms chamber 25 between membrane 13 and 17.

Figure 5:
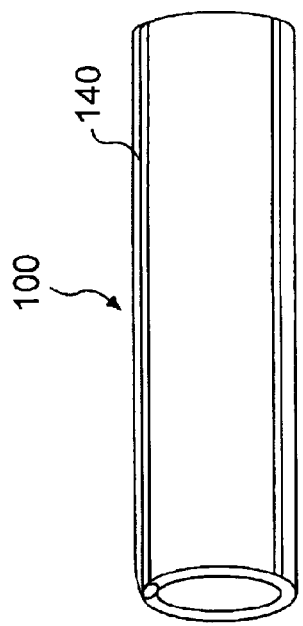
FIG. 5 is a sectional side view of a stenting system according to another embodiment of the present invention.

Stent 14 is generally a tubular member, although it may take different forms depending on the target vessel or lumen. For instance, stent 14 may have many known tubular shapes, such as an indented tube as shown in FIGS. 1 and 2. Alternatively, for example, the stent 14 could be a straight tubular member, as shown at 140 in stenting system 100 shown in FIG. 5.

Stent 14 may be any of the types well known in the art. For instance, stent 14 may be an expandable type stent that expands radially outwardly from a first position, wherein the stent passes through the body lumen or target vessel, to a second expanded position, wherein stent 14 is retained against the wall of the body lumen or other target vessel. Stent 14 may be formed from many known stent constructions, such as cross-hatched or mesh filaments or interlocking loops. The initial size of stent 14 depends on the shape and size of the target vessel. Stent 14 preferably is sized such that the stenting system can be inserted into a target vessel and can be expanded such that the stenting system is retained against the vessel wall.

Stent 14 may be expanded through known means such as by a balloon, or any other device capable of expanding stent 14, deployed through the lumen 19 of stent 14. The stenting system could be delivered to the target site over a balloon catheter. Once at the target site, the balloon could be inflated causing stent 14 to expand. The balloon may then be deflated, and stenting system 10 is retained in the lumen against the target vessel wall. When in place, blood, fluids, or other material may pass freely through lumen 19 of stent 14. In this case, stent 14 can be made from high or low molecular weight stainless steel or other suitable material.

Alternatively, stent 14 may be of the self-expanding type, that is one that has mechanical memory such that it can return to a preformed shape after it has been compressed or deformed. In such a case, the tube is initially configured in its final desired shape. The tube is then contracted by deforming the tube or by constraining the tube using any of several techniques known in the art. The tube can remain in this contracted state until it is delivered to the target vessel where it is allowed to expand to its initial state.

Further, eye holes 30 may be provided on the ends of stenting system 10, as shown in FIG. 3, providing an easy means to grasp hold of the stenting system for placement and removal. The eye holes 30 can be grasped and the stenting system elongated for placement and removal of the stenting system.

In the embodiment of a self-expanding stent, stent 14 preferably is made from an alloy having shape retaining properties such as a high or low molecular weight nickel and titanium alloys, commonly known as nitinol alloys, PLLA, PGA, or other suitable substances. Stent 14 is initially formed in its end desired shape. The shape and size of stent 14 depends on the shape and size of the target lumen or vessel. The stent 14 may be shaped such that after stenting system 10 has been inserted into the target vessel, the stenting system is slightly larger than the lumen of the target vessel so that stenting system is retained against the vessel wall.

In another embodiment of the present invention, as shown in FIGS. 6 and 7, stenting system 10 may be retained in the target vessel through use of tissue adhesives. Adhesives 33 may be applied at the ends of the stenting system, along membranes 13 or 23, preferably for a length of 0.5 to 1 micronmeter. The adhesives may be applied to membrane 13 or impregnated into membrane 23. Adhesives such as hyaluronic acid or those use on self-stick, repositionable note pads, or other suitable adhesives.

In this embodiment, the stenting system could be deployed within a sheath 36 made from a material, such as Teflon, that does not adhere to the adhesive. As shown in FIG. 8, the stenting system may be introduced to the target site with sheath 36. When sheath 36 is removed (by, for example, moving if proximally relative to the stenting system), the stenting system will expand and adhesive 33 can retain the stenting system along the vessel walls 35. The tissue adhesive may be used alone, thereby reducing the mechanical forces on the lumen, or in conjunction with other methods of retaining the stenting system in place such as balloon expanded stents or self-expanding stents to help prevent stent migration.

Stenting system 10 may be delivered to the target site with a catheter, endoscope, or other conventional delivery techniques. For instance, stenting system 10 can be delivered through the working channel of an endoscope positioned at the target lumen or organ. Stenting system 10 may be delivered with a guide wire or a balloon catheter to the target site. In the case of the balloon catheter, stenting system 10 may be delivered over the balloon and expanded by the balloon so that stenting system 10 supports the vessel or organ wall. After the stenting system 10 has been delivered, the catheter, guide wire, or other delivery mechanism may be withdrawn.

Stenting system 10 further preferably has an opening 23 at one end 21 of chamber 25 for delivering the therapeutic agent to chamber 25, as shown in FIG. 1. The other end 29 of chamber 25 is preferably sealed, but may be provided with an opening or a sealable opening. Stenting system 10 also preferably has a flexible tube 27 attached to membranes 13 and 17 at opening 23, or other delivery means in communication with chamber 25 for delivering the therapeutic agent to the chamber. It should be recognized that other delivery mechanisms could be used such as a needle inserted into a frangible member provided at opening 23. Moreover, it also should be recognized that there may be instances in which it is preferable to have delivery means connected to both ends of chamber 25, or, alternatively, to have both ends of chamber 25 sealed. If both ends of chamber 25 are sealed, the agent may be provided in the chamber prior to sealing of the chamber or the agent may be delivered into the chamber through a needle inserted into the chamber or other delivery mechanism.

The therapeutic agent of interest may be delivered to opening 23 in the stenting system 10 through flexible tubing 27, an endoscope, catheter, or other conventional delivery systems. If a single delivery of an agent is desired, such as in the case of genetic material or cancer treating agent, the delivery system can be removed after the material has been delivered. If constant delivery of a material over a period of time is desired, such as for the delivery of cellular material or a low level of medication over a period of time, the tubing 27 can be provided or other delivery system can remain docked to the stenting system to provide material delivery. Moreover, if multiple or repeated deliveries of a substance are desired, the delivery system can be re-introduced to deliver the material to opening 23.

As an alternative to leaving flexible tubing 27 or other delivery system docked at stenting system 10, and as an alternative to repeating deliveries of a therapeutic agent to stenting system 10, the therapeutic agent could be prepared such that it releases at a low level over an extended period of time. Specifically, the therapeutic agent could be mixed with an extended release polymer resulting in delivery of a low level of the agent for weeks or months or longer. One such extended release polymer is ethyl vinyl acetate which provides a good delivery medium for a polyolefin tube and causes the agent to be delivered over an extended period of time. Similarly, as discussed above, the porosity of membrane 13 may be adjusted to provide controlled release of the therapeutic agent.

Stenting system 10 also may be provided with a valve 31 located at the end of flexible tubing 27, as shown in FIG. 2, to prevent back flow of the therapeutic agent. Alternatively, valve 31 could be located directly at opening 23. The valve could be a conventional duck bill valve, elastomeric valve, or any other suitable valve. If the therapeutic agent has a high viscosity such that not much of the agent escapes through opening 23, a valve may not be necessary. On the other hand, if the therapeutic agent has a low viscosity, it may be desirable to use a valve to prevent the agent from back flowing through tubing 27 or opening 23.

Moreover, the extent to which a valve is used may depend on the agent being delivered and the delivery mechanism. In certain applications, such as with delivering an anti-inflammatory substance, it may not be critical to prevent the escape of the therapeutic agent through opening 23. Whereas in other applications, such as with cancer fighting agents, it may be more desirable to prevent the escape of any of the agent through opening 23. In addition, certain delivery mechanisms may have means to prevent any escape of the agent through opening 23, and in such instance a valve would be unnecessary.

The stenting system of the present invention may be used in a number of situations. For example, it may be used in the replacement of abnormal or damaged cells in the alimentary and/or pulmonary tracts, such as in the case of Barrett's esophagus. In such a treatment, the abnormal cells are killed or removed from the tissue and normal cells are cultured and delivered to the diseased or damaged site in an effort to regrow normal cell tissue. The stenting system of the present invention may be used both to remove the abnormal cells and to deliver the cultured cells to the site.

Stenting system 10 may be delivered to the target site with an agent that will remove or burn off the surface layer of cells in the abnormal region. Normal cells that have been cultured and mixed with a growth medium may then be introduced into the port in the stenting system and into the material holding chamber. The cells are then delivered through porous outer tube directly to the damaged body tract to enhance healing and new normal cell growth. Stenting system 10 also provides a protective environment to allow the cells to grow back as a normal cell type. Further, stenting system 10 allows for the passage of other materials, such as food, through the lumen 19 of the stent 14 and can therefore be used in place for an extended period of time.

Stenting system 10 may also be used to repair damaged cellular membranes as a result of chemicals, chemotherapy, radiation, or inhalation of toxic compounds. The stenting system may also be used to deliver a drug to a body site. The stenting system of the present invention is not limited to the applications specifically described herein but may be used in a number of other situations.

It will be apparent to those skilled in the art that various modifications and variations can be made to the structure and methodology of the present invention without departing from the scope or spirit of the invention. In view of the foregoing, it is intended that the present invention cover modifications and variations of this invention that fall within the scope of the following claims and their equivalents.

What is claimed is:

1. A system for insertion into a body lumen for delivering an agent to a site on the body lumen, the system comprising, a tubular member having a lumen there through to allow the passage of material, wherein the tubular member may be expanded causing the stenting system to be retained against the wall of the body lumen;

an outer membrane surrounding the tubular member, wherein at least a portion of the outer membrane is porous to the agent to allow the agent to be deposited on the site;

an inner membrane attached to the tubular member, wherein the inner membrane is non-porous to the therapeutic agent to be delivered to the site; and a chamber located between the inner and outer membranes for holding the agent, wherein the agent in the chamber diffuses through the porous portion of the outer membrane and onto the body site.

2. The system according to claim 1, further comprising an opening in the chamber for delivery of the agent to the chamber.

3. The system according to claim 2, further comprising a one-way valve in the opening preventing the agent from exiting the chamber through the valve.

4. The system according to claim 1, wherein the inner membrane prevents the agent in the chamber from entering the lumen of the tubular member.

5. The system according to claim 1, wherein the tubular member is formed from a material that can return to its initially formed shape after deformation.

6. The system according to claim 1, wherein the tubular member is capable of being expanded by a balloon inserted into the lumen of the tubular member.

7. The system according to claim 1, wherein the outer membrane is flexible such that it may conform to the shape of the body lumen.

8. The system according to claim 1, further including a tubing in communication with the chamber for introducing to the agent into the chamber.

9. A system for insertion into a body lumen for delivering an agent to a site on the body lumen, the system comprising,
an inner tubular member having a lumen there through for the passage of material;
a membrane surrounding the inner tubular member;
an outer tubular member surrounding the inner tubular member and the membrane; and
a porous member forming at least a portion of the outer tubular member, wherein the membrane and the outer tubular member define a chamber there between for holding the agent, wherein the agent in the chamber may pass through the porous member of the outer tubular member and be deposited directly on the body site, and wherein the membrane is non-porous to the agent thereby isolating the lumen of inner tubular member from the agent in the chamber.

10. The system according to claim 9, further comprising balloons located at each end of the outer tubular member, wherein the balloons can be expanded to retain the system against a wall of the lumen.

11. The system according to claim 9, wherein the inner tubular member is capable of being expanded such that when it is expanded the system is retained against the lumen wall.

12. The system according to claim 11, wherein the inner tubular member is formed from a material that can return to its initially formed shape after deformation.

13. The system according to claim 11, wherein the inner tubular member is capable of being expanded by a balloon inserted into the lumen of the inner tubular member.

14. The system according to claim 9, further including a tubing in communication with the chamber for introducing the agent into the chamber.

15. The system according to claim 9, further comprising an opening in the chamber for delivery of the agent to the chamber.

16. The system according to claim 11, further comprising a one-way valve in the opening preventing the agent from exiting the chamber through the valve.

17. A system for delivering an agent to a body site comprising:
an expandable tube having a lumen there through, wherein the sides of the tube have openings therein to allow passage of material through the lumen;
an outer membrane surrounding the expandable tube and forming a chamber with a surface of the expandable tube, wherein at least a portion of the membrane is porous to the agent allowing diffusion of the agent there through to the body site, and wherein the expandable tube prevents the agent from diffusing from the chamber and into the lumen of the expandable tube; and
an opening in the chamber allowing delivery of the agent to the chamber.

18. The according to claim 17, further comprising an inner membrane attached to the expandable tube, wherein the inner membrane is non-porous to the agent and prevents the agent in the chamber from entering the lumen.

19. The system according to claim 17, further comprising a one-way valve located in the opening preventing the agent from exiting the chamber through the valve.

20. The system according to claim 17, wherein the tube is formed from a material that can return to its initially formed shape after deformation.

21. The system according to claim 17, wherein the tube is expanded against the body site by a balloon catheter introduced through the lumen of the inner tube.

22. The system according to claim 17, further comprising tissue adhesives located along a portion of the tube for retaining the tube at the body site.

* * * * *

UNITED STATES PATENT AND TRADEMARK OFFICE
CERTIFICATE OF CORRECTION

PATENT NO. : 6,939,374 B2
DATED : September 6, 2005
INVENTOR(S) : Michael S. Banik et al.

It is certified that error appears in the above-identified patent and that said Letters Patent is hereby corrected as shown below:

Title page,
Item [74], *Attorney, Agent, or Firm*, delete the comma after "Garrett".
Item [57], ABSTRACT,
Line 3, after "includes", delete "an".
Line 4, "there through" should read -- therethrough --.

Column 8,
Line 53, "there through" should read -- therethrough --.

Column 9,
Line 24, "there through" should read -- therethrough --.
Line 32, "there between" should read -- therebetween --.

Column 10,
Line 13, "claim 11," should read -- claim 9, --.
Lines 23-24, "there through" should read -- therethrough --.
Line 29, "The according to claim 17," should read -- The system according to claim 17, --.

Signed and Sealed this

Eighth Day of November, 2005

JON W. DUDAS
*Director of the United States Patent and Trademark Office*